United States Patent [19]

Kinnamon

[11] 4,209,519
[45] Jun. 24, 1980

[54] ANTI-LEISHMANIAL LEPIDINE DERIVATIVES

[75] Inventor: Kenneth E. Kinnamon, Silver Spring, Md.

[73] Assignee: The United States of America as represented by the Secretary of the Army, Washington, D.C.

[21] Appl. No.: 886,024

[22] Filed: Mar. 13, 1978

[51] Int. Cl.$^2$ ............................................. A61K 31/47
[52] U.S. Cl. ..................................... 424/258; 546/171
[58] Field of Search ........................ 546/171; 424/258

[56] References Cited

U.S. PATENT DOCUMENTS

| | | | |
|---|---|---|---|
| 2,508,937 | 5/1950 | Campbell | 546/171 |
| 3,142,679 | 7/1964 | Barrett et al. | 544/363 |

FOREIGN PATENT DOCUMENTS 826811  1/1960  United Kingdom ..................... 546/171

OTHER PUBLICATIONS

Shetty et al., J. of Med. Chem. (1977), vol. 20, #10, pp. 1349–1351.
Beveridge et al., "Nature", vol. 182 (1958), pp. 316–317.
Shetty et al., J. of Med. Chem. vol. 21, #9 (1978), pp. 995–998.
La Montagne et al., J. Med. Chem. vol. 20, #9 (1977), pp. 1122–1125.

*Primary Examiner*—Allen J. Robinson
*Attorney, Agent, or Firm*—William G. Gapcynski; Werten F. W. Bellamy; Sherman D. Winters

[57] ABSTRACT

The subject 8-amino-6-methoxy lepidine derivatives have the formula:

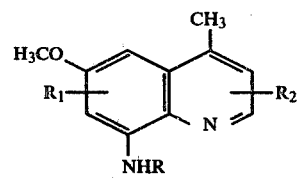

wherein, R represents an —alkylene (tertiary) amine, —alkylene-NH$_2$, [(N-alkylsubstituted piperadyl amino)-alkylene-, —alkylene-(tertiary) amine or —alkylene-N-heterocyclic; R$_1$, represents an alkoxy, alkyl, halogenated alkyl, alkenyl, aryloxy, halogen or hydrogen radical; R$_2$ represents an alkyl, halogenated alkyl or aryloxy; n represents integers 3, 4, 5, 6 or 7; and pharmaceutically acceptable salts thereof wherein the salt forming acid or acid-hydrate is organic or inorganic. These derivatives afford improvement in means for the chemotherapy of leishmaniasis. Presence of a basic side-chain attachment at position 8- provides means for enhancement of the effectiveness of such compounds, which may be administered parenterally or orally to infected animals.

19 Claims, No Drawings

ANTI-LEISHMANIAL LEPIDINE DERIVATIVES

The invention described herein may be manufactured and used by or for the Government for governmental purposes without payment of any royalty thereon.

BACKGROUND OF THE INVENTION

1. Field of the Invention

The invention generally relates to the chemotherapy or treatment of leishmaniasis and, more specifically, relates to the parenteral or oral administration of 8-amino-6-methoxyl lepidine derivatives as a means for the chemotherapy of leishmaniasis.

2. Description of the Prior Art

Leishmania are well known intra-cellular protozoan parasites which may give rise to serious infections in man. The organisms are transmitted by the "bite" of an infected sandfly, and invade the reticulo-endothelial system (RES). The parasites are highly successful in their ability to grow and multiply in the very tissues of the vertebrate host which are responsible for reaction to invading organisms. Expectedly, such location of Leishmania renders difficult a satisfactory approach to chemotherapy, and there is highly complex inter-play between parasites and cellular immune responses of the host. When Leishmania invade visceral aspects of the RES (spleen and liver, in particular), death is the common result of untreated infections. Consequences of leishmanial infections of muco-cutaneous tissues are considerably less severe, and cutaneous leishmaniasis is very rarely life-threatening in nature. There are considerable differences in response of various animals to leishmanial infections. A satisfactory animal model for laboratory trials has been found in *Leishmania donovani* infections in the golden hamster. In man, that parasite causes a visceral leishmaniasis which is usually fatal.

The *L. donovani*-hamster model has been used widely to assess candidate drugs for anti-leishmanial effects. Unfortunately, relatively few drugs have been found to show appreciable activity on screening, and fewer yet have merited trial in man. Pentavalent compounds of antimony have become mainstays for treatment of human leishmaniasis, despite liabilities of toxic side-effects. Of the antimonial drugs, one widely used in the clinic is the N-methyl glucamine salt of antimonic acid, frequently called meglumine antimoniate. That compound has been presently employed as a reference drug in evaluation of compounds in the *L. donovani*-hamster test.

SUMMARY of the INVENTION

Quinoline derivatives are known to have chemotherapeutic effects against diverse parasites of man. Especially noteworthy potency aganist malaria parasites has been demonstrated among 4-aminoquinoline and 8-aminoquinoline structures.

According to this invention, it has been established that certain lepidine derivatives possess novel and marked anti-leishmanial effects in the *Leishmania donovani*-hamster test.

Quinoline derivatives which have been effectively administered in accordance with the method of this invention are represented by the formula.

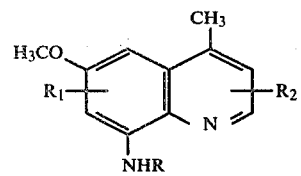

wherein R represents an —alkylene (tertiary) amine, —alkylene-$NH_2$, (N-alkyl substituted piperidyl amino) alkylene-, —alkylene (tertiary) amine, or —alkylene N-heterocyclic; $R_1$, represents an alkoxy, alkyl, halogenated alkyl, alkenyl, aryloxy, halogen or hydrogen radical; $R_2$ represents an alkyl, halogenated alkyl or aryloxy; n represents integers 3, 4, 5, 6 or 7; and pharmaceutically salts thereof wherein the salt forming acid or acid-hydrate is inorganic or organic in nature. Certain representatives have shown potency many hundred times that of meglumine antimoniate, and provide a unique advance in the chemotherapy of leishmaniasis. For example, the presence of the lepidine structure was crucial to the exceptional and unexpected high levels of effectiveness obtained from compounds represented by the structural formula

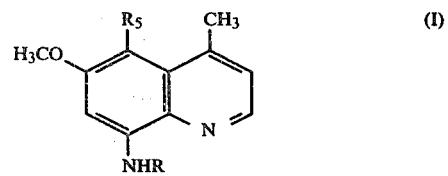

where R represents a basically-substituted alkyl grouping containing less than 10 carbon atoms in 2 straight or branched chain and $R_5$ is H or a lower alkoxy function. The basic substituent attached to the alkyl chain may consist of a primary, or a secondary, or a teritiary amino grouping which may or may not be a part of an heterocyclic moiety. Alkyl, or substituted alkyl, groupings may be selected as functions for attachment to the basic nitrogenous moiety.

Lepidine derivatives of the type illustrated by structure (I) may be administered perorally or parenterally to achieve anti-leishmanial effects. For convenience, such drugs may be administered in the form of the neat chemical basis or as a salt of a pharmaceutically acceptable acid, either inorganic or organic in chemical nature. Non-restrictive examples of inorganic acids suitable for preparation of salts of structure (I) include: hydrochloric acid; phosphoric acid; nitric acid; sulfamic acid; and sulfuric acid. Suitable organic acids which may be used to form salts of structure (I) include the following, non-restrictive examples: maleic acid; fumaric acid; citric acid; beta-resorcylic acid; and pamoic acid.

When administered in oral dosage forms, subject anti-leishmanial agents may be incorporated into tablets (single or multi-layer, coated or uncoated), capsules, dragées, and the like. The formulation of such oral dosage forms may advantageously include optional excipients such as lactose, precipitated chalk, dibasic calcium phosphate, microcrystalline cellulose derivatives, maize starch, talc, calcium stearate, or like adjuvant substances whose identity and use are well known in pharmaceutical compounding art. For peripheral administration, aqueous or oily solutions of these lepidine derivatives may be used in a wide range of concentrations. In certain instances, advantage may be gained with use of aqueous suspensions such as may be obtained with ethoxylated sorbitan fatty acid esters, optionally with addition of thickeners such as carboxymethyl cellulose or polyethylene glycol.

DESCRIPTION OF THE PREFERRED EMBODIMENT

The synthesis of anti-leishmanial agents of structure (I) finds basis in chemical art involving reaction of an 8-aminoquinoline with RX (X being an halogen, usually Cl, Br, or I) to produce the desired 8-NHR quinoline, or by kindred process for conveniently obtaining a basically-substituted side-chain. In certain cases, 8-amino group may be more conveniently interacted with an acid chloride type to form an amide, then the amide carbonyl function reduced. Embodied in the copending patent application Ser. No. 774, 165 (Mar. 3, 1977) now U.S. Pat. No. 4,167,638, are improvements in the process for obtaining 8-NHR quinolines, including structure (I).

Methods

Assessment of anti-leishmanial effects was done in a model test system based on work of Stauber, et al. [J. Protozool., 5, 269–273 (1958)].

Male golden hamsters (*Mesocricetus auratus*), weighing approximately 50–60 gm and the Khartoum strain of *Leishmania donovani* were used in this work. Suspensions of amastigotes for the inoculation of experimental hamsters were prepared by grinding heavily infected hamster spleens in Hank's balanced salt solution in a Ten Broeck tissue grinder and diluting the suspension to contain $10^7$ amastigotes per 0.2 ml, the amount inoculated into each hamster via the intracardial route. Administration of the drug was initiated 3 days after inoculation and continued through day 6. One day later, the hamsters were weighed, killed, their livers removed and weighed. Liver impressions were prepared, stained with Giemsa's stain and the ratio of the number of amastigotes per host liver cell nucleus determined.

In preparation for the initiation of therapy, the hamsters were weighed and apportioned into groups of 6 to 8. Test compounds were prepared in 0.1% Tween ® 80 plus 0.5% hydroxyethylcellulose (HEC-Tween ®) and administered twice daily on days 3 through 6 via the intramuscular, subcutaneous, or oral routes. Compounds were tested at 3 drug dose levels, generally 208, 52 and 13 milligrams per kilogram body weight per day. A group containing a minimum of 6 hamsters was used for each drug dosage level of each test compound. At the time of testing the identity of compounds evaluated was unknown, i.e., compounds were tested "blind". Also included in each experiment was the reference compound, N-methylglucamine antimoniate (commercially known as Glucantime ®), at drug dose levels of 104, 13 and 3.25 mg of Sb/kg/day.

Comparison of the suppressive effects of the test compounds with that of the reference compound was made from parasite densities in the liver of each hamster. Total number of parasites in the liver of each hamster were determined from liver impressions according to the method of Stauber et al., 1958.

When the ratio of the number of amastigotes to the number of liver cells had been determined for each hamster in all experimental groups, this data along with initial and final body weights were evaluated with the aid of an IBM 360 computer. A program was devised in which the raw data were accepted by the computer and the total and mean numbers of amastigotes per liver, per cent suppression of numbers of amastigotes, and percent body weight change were calculated. Significance tests on the percent suppression of amastigotes were done. The calculations allowed a comparison of the total numbers of amastigotes in the liver of each hamster receiving the reference of test compounds with the mean number of amastigotes in the livers of controls.

A comparison of the anti-leishmanial activity of each test compound with that of the reference compound was made and a meglumine antimoniate index (relative activity of the test compound to that of the reference drug, which is also called Glucantime ®) for each test compound was calculated by the following formula:

$$\text{Glucantime } \textcircled{R} \text{ index } (G) = \frac{SD_{90} \text{ for Glucantime } \textcircled{R}}{SD_{90} \text{ for test compound}}$$

For antimony containing compounds, the comparison was based upon the weight of antimony; for non-antimonial containing drugs the comparison was made based upon the total molecular weight of the compound less that fraction attributable to the salt. The drug dosage levels of active test compounds required for a given degree of effect such as 90% suppression ($SD_{90}$) was estimated graphically by plotting percent parasite suppression vs. milligrams of compound administered per kilogram body weight of the hamster on log paper. When the $SD_{90}$ value could not be obtained because of low activity of the test compound, a lower SD value was used. A G value of greater than one indicates that the test compound was more active than the reference compound, meglumine antimoniate.

The percentage weight gain or loss of treated animals was used as a crude indication of the toxicity of the compound. In addition, the hamsters were observed daily for clinical signs of toxicity such as roughened hair coat, nervous disorders, and death. At necropsy, gross lesions were noted. All of these criteria were used in the determination of the toxicity of the test compound.

The relatively high degree of reproducibility of the screening procedure can be seen fron the followng data. After 39 weekly experiments, the mean number of amastigotes in the livers of control hamsters was found to be $5.11 \times 10^8$ ($\pm 10^7$ at 95% confidence). Equally good reproducibility was obtained from hamsters receiving 104, 13, or 3.25 mg/kg/day of the reference compound, meglumine antimoniate. The mean number of amastigotes in the livers of these hamsters were $12.1 \times 10^7$ ($\pm 1.1 \times 10^6$), $1.57 \times 10^8$ ($\pm 11.6 \times 10^6$) and $3.5 \times 10^8$ ($\pm 1.30 \times 10^9$). These represents suppressions of 97.6%, 69.2% and 38.3% respectively for the three drug dosage levels.

EXAMPLES

The following examples illustrate without any implied limitation, the practice of this invention.

Diverse 8-amino-6-methoxyquinoline derivatives available from an antimalarial program prompted study of the compounds as anti-leishmanial agents against *Leishmania donovani* infections in the golden hamster, *Mesocricetus auratus*. Prior workers had established the worth of the model test system, and others indicated that 8-amino-6-methoxyquinoline types possess antileishmanial effects. The Examples are presented in tabular form to give evidence of the unique effectiveness of lepidines (4-methylquinolines) as antileishmanial agents. Table I covers Examples 1–23, which are variously substituted 8-(4-amino-1-methylbutylamino)-6-methoxyquinolines and their testing. Examples 24–35 in Table II are 6-methoxylepidines having variations in basic function as NHR at position 8-, together with activity against *L. donovani* in the golden hamster. Table III lists Examples 36–50, together with anti-leishmanial testing data.

Table I shows that presence of a methyl grouping at position 4- of primaquine analogues produces marked enhancement in anti-leishmanial effectiveness. Table II provides comparison of anti-leishmanial profiles of various 8-substituted 6-methoxy-lepidines. Thus, comparison of the effects of the terminal amino function (primary; secondary; and tertiary) and chain length upon anti-leishmanial activity is possible. Example 34 points to the noteworthy effectiveness of the 6-methoxy lepidine type bearing an 8-(6-diethylaminohexylamino) grouping. Table III gives further evidence of anti-leishmanial potency of lepidine derivatives.

Table I 8-(4-Amino-1-methylbutylamino)-6-methoxyquinolines:
Activity Against *Leishmania donovani* Infections of Hamsters

[Structure: 6-methoxyquinoline with positions 2,3,4,5,7 labeled, and 8-NH—CH(CH$_3$)—(CH$_2$)$_3$NH$_2$ group]

| Example Number[a] | 2 | 3 | 4 | 5 | 7 | G[b] |
|---|---|---|---|---|---|---|
| 1 | | | | | | 2.1 |
| 2 | —CH$_3$ | | | | | 6.8 [9.8][c] |
| 3 | | —CH$_3$ | | | | 12.1 |
| 4 | | | —CH$_3$ | | | 32.7 [34.8][c] |
| 5 | —CH$_3$ | | | —CH$_3$ | | 9.6 |
| 6 | | | | | —CH$_3$ | <1[d] |
| 7 | —CH$_3$ | —CH$_3$ | | | | 20.2 |
| 8 | —OCH$_3$ | | | | | 3.4 |
| 9 | | | —OCH$_3$ | | | 1.6 |
| 10 | | | | | —OCH$_3$ | 2.1 |
| 11 | —CF$_3$ | | | | | NA (13)[e] |
| 12 | | | —CF$_3$ | | | 2.0 |
| 13 | —C$_2$H$_5$ | | | | | 14.0 |
| 14 | | | —C$_2$H$_5$ | | | 31.3 |
| 15 | —CH=CH$_2$ | | | | | 1.9 |
| 16 | | | —CH=CH$_2$ | | | 8.5 |
| 17 | | | —CH=CHCH$_3$ | | | 5.3 |
| 18 | | | —CH=CHCH$_2$CH$_3$ | | | 0.5 |
| 19 | | | —(CH$_2$)$_2$CH$_3$ | | | 6.2 |
| 20 | | | —(CH$_2$)$_3$CH$_3$ | | | 1.3 |
| 21 | | | —CH$_2$OH | | | NA (3.25) |
| 22 | | | —NH$_2$ | | | NA (13) |
| 23 | | | —OH | | | NA (3.25) |

[a]CHEMICAL FORM: Example 1,4,6,10: diphosphate; Examples 2,23: tetrahydrochloride (monohydrate); Example 3: tetraphosphate (trihydrate); Examples 5,12,15,17,19,21: fumarate; Example 7: tri (beta-resorcylate); Examples 8,13: (Mono)maleate; Examples 9,11: (mono) phosphate; Example 14: dihydrobromide; Example 18: difumarate; Example 22: diphosphate trihydrate.
[b]G index is the relative activity of the test compound to that of meglumine antimoniate.
[c]Except for those within [ ] all values shown were obtained after intramuscular administration of the compound. Those within [ ] were observed after oral administration.
[d]<1 indicates that activity was observed but the activity was less than for the standard drug, meglumine antimoniate. At 104, 13, and 3.25 mg/kg/day meglumine antimoniate is respectively approximately 95%, 70% and 40% suppressive.
[e]NA means that the compound was not found to be active. Numbers within () designate highest dose level tested in mg/kg/day.

Table II

8-Substituted-6-methoxy-lepidines:
Activity Against *Leishmania donovani* Infections of Hamsters

[Structure: 4-methyl-6-methoxyquinoline with 8-NHR substituent]

| —NHR Series[a] | G[b] Index n | | | | | |
|---|---|---|---|---|---|---|
| | 3 | 4 | 5 | 6 | 7 | 8 |
| Series 1: —NH(CH$_2$)$_n$NH$_2$ | | | | | | |
| Example 24: n=3; Example 25: n=4; | | | | | | |
| Example 26: n=5; Example 27: n=6. | 1.9 | 8.1 | 41.4 | 6.5 | | |
| Series 2: —NH(CH$_2$)$_n$NHCH(CH$_3$)$_2$ | | | | | | |

Table II-continued

8-Substituted-6-methoxy-lepidines:
Activity Against *Leishmania donovani* Infections of Hamsters

| —NHR Series[a] | G[b] Index n | | | | | |
|---|---|---|---|---|---|---|
| | 3 | 4 | 5 | 6 | 7 | 8 |
| Example 28: n=3; Example 29: n=5; | | | | | | |
| Example 30: n=6; Example 31: n=7; | | | | | | |
| Example 32: n=8. | | 16.2 | 219 | 383 | 137 | 27.0 |
| Series 3: —NH(CH$_2$)$_n$N(C$_2$H$_5$)$_2$ | | | | | | |
| Example 33: n=5; Example 34: n=6; | | | | | 474 | |
| Example 35: n=7. | | | 282 | [708][c] | 117 | |

[a]CHEMICAL FORM: Examples 24, 27, 28, 29, 31, 34, 35: dihydrochloride; Examples 25, 26, 31: diphosphate; Example 33: (mono)citrate; Example 30: dihydrochloride (mono)hydrate; Example 32: dihydrochloride dihydrate.
[b]G index is the relative activity of the test compound to that of meglumine antimoniate.
[c]Except for the compound within [ ] all values shown were obtained after intramuscular administration of the compound. The compound within [ ] was observed after oral administration.

Table III 8-(6-Diethylaminohexylamino)quinolines:
Activity Against *Leishmania donovani* Infections of Hamsters

| Example Number | Position of Substituent | | | | | G[b] |
|---|---|---|---|---|---|---|
| | 2 | 3 | 4 | 5 | 6 | |
| 36 | | | | | | < 1[c] |
| 37 | | | | | OCH$_3$ | 3.5 |
| 38 | | | | | Cl | NA (3.25)[d] |
| 39 | | | | Cl | OCH$_3$ | 1.1 |
| 34 | | | —CH$_3$ | | OCH$_3$ | 474 [708][d] |
| 40 | | | —CH$_3$ | | | < 1 |
| 41 | —CH$_3$ | | | | | NA (3.25)[e] |
| 42 | | | CH$_3$ | F | —OCH$_3$ | 66.1 |
| 43 | | | —CH$_3$ | —OCH$_3$ | —OCH$_3$ | 401 |
| 44 | —C$_2$H$_5$ | | CH$_3$ | | OCH$_3$ | 130 |
| 45 | | | —C$_2$H$_5$ | | —OCH$_3$ | 44.9 |
| 46 | —CH$_3$ | | —C$_2$H$_5$ | | —OCH$_3$ | 29.2 |
| 47 | | | | | —OCH$_3$ | 4.2 |
| 48 | | | —O—Ph / —CF$_3$ | | —OCH$_3$ | 21.4 |
| 49 | —CHBrCH$_3$ | | CH$_3$ | | —OCH$_3$ | 2.6 |

[a]CHEMICAL FORM: Example 36, (mono)citrate; Example 37, (mono)phosphate; Example 38, (mono)oxalate; Example 39, base; Examples 40, 42, 43, 44, dihydrochloride; Examples 34, 41, dioxalate; Examples 45, 46, dihydrobromide; Example 47, (mono)hydrochloride; Example 48, dicitrate (mono)hydrate; Example 49, (mono)hydrobromide.
[b]G index is the relative activity of the test compound to that of meglumine antimoniate.
[c]<1 indicates that activity was observed but the activity was less than shown by the standard drug, meglumine antimoniate. At 104, 13, and 3.25 mg/kg/day meglumine antimoniate is respectively approximately 95%, 70% and 40% suppressive.
[d]Except for those within [ ] all values shown were obtained after intramuscular administration of the compound. Those within [ ] were observed after oral administration.
[e]NA means that the compound was not found to be active. Numbers within ( ) designate highest dose level tested in mg/kg/day.

EXAMPLE 50

8-[6-(1-Ethyl-3-piperidylamino)hexylamino]-6-methoxyquinoline

Testing of the di-beta-resorcylate monohydrate of 8-[6-(1-ethyl-3-piperidylamino)hexylamino]-6-methoxyquinoline was done in the *L. donovani*-golden hamster model. The value for G was 6.7.

A. 6-Methoxy-8-(6-phthalimidohexylamino) quinoline

A mixture of 6-methoxy-8-aminodquinoline (30.72 g, 0.1764 mol), 6-bromohexylphthalimide (35.82 g, 0.1155 mol) and propanol-2(70 ml) was stirred and placed in an oil bath preheated at 80°. The temperature was raised to 125° in 0.5 hr and kept at 125°–130° for an additional 2 hrs. The melt was cooled and extracted with hot benzene. Insoluble 6-methoxy-8-amino-quinoline hydrobromide was removed by filtration and the filtrate concentrated in vacuo. The residual gum was crystallized from acetone to give 26.87 g (75%) of the product, mp 123°–124°, lit. mp. 126°–127° [Elderfield, et al., J. Am. Chem. Soc., 68, 1568 (1946)].

B. 8-(6-Aminohexylamino)-6-methoxyquinoline

A mixture of 6-methoxy-8-[(6-phthalimidohexyl)amino]-quinoline(8.07 g, 0.02 mol), hydrazine hydrate 100% (1.10 g, 0.022 mol) and ethanol (175 ml) was refluxed for 17 hrs. It was then evaporated under reduced pressure. The solid residue, mixed with a solution of 10 ml of concentrated hydrochloric acid in 150 ml of water was refluxed for 5 min, cooled and filtered. The dark red filtrate was evaporated to a solid which was recrystallized from ethanol to give 7.02 g of dihydrochloride salt, mp 185° decomposition. A 1 g sample recrystallized once more from ethanol, gave a 0.92 g crop, mp 188° (decomposition.), lit. mp. 180°–190°. [Elderfield, et al., J. Am. Chem. Soc., 68, 1568 (1946)].

C. 8-[6-(1-Ethyl-3-piperidylamino)-hexylamino]-6-methoxyquinoline

A mixture of 6-methoxy-8-(6-aminohexylamino)-quinoline dihydrochloride (4.16 g, 0.012 mole), 1-ethyl-3-piperidone hydrochloride (3.3 g, 0.02 mole), triethylamine (6.06 g, 0.06 mole) and 75 ml ethanol was briefly warmed to 50° to obtain a clear solution, cooled to room temperature, mixed with 0.5 g to $PtO_2$ and hydrogenated at room temperature and pressure. The mixture was warmed, filtered, concentrated in vacuo, and the residue taken up in a minimal amount of cold water. The base was liberated in the cold with solid sodium hydroxide, and extracted with ether. After drying ($K_2CO_3$) the extracts, the solvent was removed, and the residual dark oil de-gassed (70°/0.05 mm) to remove any decomposition products from 1-ethyl-3-piperidone. To purify the crude base, it was expedient to dissolve it in ether and chromatograph it on alumina. Thereby, 3.5 g of an oily yellowish material was obtained after removal of solvent. It was converted into the beta- resorcylate salt in ether and dried well (56°, at 0.01 mm.) The yellowish salt (4.1 g.) showed the following behavior upon heating: shrinking, 64°; melting, 85°; decomposition, 122°.

Anal., Calcd. for $C_{23}H_{36}N_4O \cdot 2 C_7H_6O_4 \cdot 1 H_2O$ (MW 710.8); C, 62.51; H, 7.09; N, 7.88. Found: C, 62.08. 62.12; H, 7.21, 6.89; N, 7.88, 7.99. MW by titration: Calcd, 710.8; Found, 707.1.

EXAMPLE 51

8-{-[4-(2-Hydroxyethyl)-1-piperazinyl]ethylamino}-6-methoxy-4-methylquinoline

The dimaleate of 8-2-[4-(2-hydroxyethyl)-1-piperazinyl]ethylamino-6-methoxy-4-methylquinoline was isolated as a one-fourth hydrate, as described below. It was evaluated for anti-leishmanial effects in the model test system and determined to have a G index of 6.3.

A. 8-{2-[4-(2-Hydroxyethyl)-1-piperazinyl]acetamido}-6-methoxy-4-methylquinoline 8-Amino-6-methoxy-4-methylquinoline was chloracetylated in acetone, in the presence of anhydrous sodium carbonate. Then, a mixture of 15.0 g (0.057 mol) of the resultant 8-chloroacetamido -6-methoxy-4-methylquinoline was suspended in 50 g triethylamine, and stirred well while there was added 8 g 1-(2-hydroxyethyl) piperazine. The mixture was heated 20 hours at 115°–120°, cooled, and quenched in cold water. The resulting tan solid was collected, then crystallized from ethanol-water (charcoal). There resulted 84—84% yields of creamy product, m.p. 126°–128°.

Anal. Calcd. for $C_{19}H_{26}N_4O_3 \cdot \frac{3}{4} H_2O$: C, 61.35; H, 7.45; N, 15.06. Found: C, 61.27, 61.35; H, 7.09, 7.13; N, 15.12, 15.07.

B. 8-{2-[4-(2-Hydroxyethyl)-1-piperazinyl]ethylamino}-6-methoxy-d4-methylquinoline To a stirred suspension of 16.2 g (0.045 mol) of the amide from A in 50 ml. dioxan, there was added 50 ml dihydropyran, and then a few mg of p-toluenesulfonic acid. The stirred mixture was heated 4 hours at 85°, then refluxed for 18 hours. The mixture was stripped of solvents in vacuo, and the residue crystallized from dioxan-hexane mixture. There resulted 14.5 g solid, the tetrahydropyranyl derivative of the OH function.

A suspension of 9.0 g lithium aluminum hydride in 500 ml tetrahydrofuran was stirred under nitrogen at 0°. To that, there was slowly added 13.0 g (0.029 mol) of the aforementioned tetrahydropyran derivative. The yellowish-green mixture was stirred at 0° for 1 hour, then at ambient temperature for 1 hour, and finally refluxed for 18 hours. After cooling, the mixture was poured into aqueous sodium hydroxide (excess), filtered, and the layers separated. The orange-yellow organic layer was dried ($Na_2SO_4$) and concentrated in vacuo. The orange oil was dissolved in 50 ml of 6 N HCl, stirred, filtered, the filtrates basified ($NH_4OH$), and the product taken up in methylene chloride. Following drying of the extracts ($MgSO_4$), the solvent was removed. The base was dissolved in ethanol to form the dimaleate. A yield of 15.6 g of yellow solid resulted. The compound was recrystallized from ethanol to afford pure dimaleate salt, m.p. 150–151°.

Anal. Calcd. for $C_{19}H_{28}N_4O_2 \cdot 2C_4H_4O_2 \cdot \frac{1}{4} H_2O$: C, 55.81; H, 6.33; N, 9.64. Found: C, 55.85; 55.88; H, 6.44, 6.44; N, 9.19, 9.18.

EXAMPLE 52

8-{6-[4/(2-Hydroxyethyl)-1-piperazinyl]hexylamino}-6-methoxy-4-methylquinoline

The tris hydrochloride of the above-named compound was subjected to evaluation in L. donovani infections in Mesocricetus auratus. It was found to have a G index of 77.8.

A. 6-Bromo-N-(6-methoxy-4-methyl-8-quinolinyl)hexanamide

To a mixture of 9.4 g (0.05 mol) of 8-amino-6-methoxy-4-methylquinoline and 8.7 g (0.082 mol) of anhydrous sodium carbonate in 60 ml of acetone was added dropwise a solution of 6-bromohexanoylchloride in 35 ml of acetone. The mixture was heated under reflux for 4 hours, cooled and filtered. The filter cake was washed with with chloroform and the filtrate and wash were combined and concentrated in vacuo to dryness. The residual solid was recrystallized first from ethanol and then from 85% aqueous ethanol to give 10.8 g (61%) of product, mp 111°–113°.

Anal. Calcd. for $C_{17}H_{21}BrN_2O_2$: C, 55.89; H, 5.80; N, 7.67; Br, 21.88. Found: C, 56.19; H, 5.53; N, 7.71; Br, 21.73.

B.
4-(2-Hydroxyethyl)-N-(6-methoxy-4-methyl-8-quinolinyl)-1-piperazinehexanamide A mixture of 7 g (0.019 mol) of 6-bromo-N-(6-methoxy-4-methyl-8-quinolinyl)hexanamide and 4.4 g (0.038 mol) of hydroxyethylpiperazine in 100 ml of benzene was heated under reflux for 48 hours, allowed to cool, mixed well with 50 ml of water and filtered to collect the crude product. Recrystallization from toluene with hexane afforded 5.7 g (72%) of crystalline material, mp 88°–90°.

Anal. Calcd for $C_{23}H_{34}N_4O_3$: C, 66.64; H, 8.27; N, 13.52. Found: C, 66.88; H, 7.88; N, 13.21.

C.
8-{6-[4-(2-Hydroxyethyl)-1-piperazinyl]hexylamino}-6-methoxy-4-methylquinoline A cold mixture (−60°) of 2.2 g (0.017 mol) of aluminum chloride in 60 ml of tetrahydrofuran was added to a mixture of 1.9 g (0.05 mol) of lithium aluminum hydride in 50 ml of tetrahydrofuran at −30°. When the mixture had warmed to −20°, a solution of 5.2 g (0.0126 mol) of the above-described hexanamide in 150 ml of tetrahydrofuran was added dropwise. The mixture was stirred for 4 hours, during which time it warmed to room temperature. To the mixture was added slowly 8 ml of 30% sodium hydroxide and then enough water to clarify the supernatant. The mixture was filtered and the filtrate concentrated to dryness in vacuo. The solid hydrochloride, which was obtained by trituration with a 19% solution of hydrogen chloride in propanol-2, was collected and recrystallized from a 6:1 mixture of ethanol:methanol to give 4.2 g (65%) of the title compound, mp 243°–245° (decomposition).

Anal. Calcd. for $C_{23}H_{36}N_4O_2 \cdot 3HCl \cdot 0.5H_2O$: C, 53.99; H, 7.84; N, 10.95; Cl, 19.40; $H_2O$: 1.76. Found: C, 54.10; H, 7.55; N, 10.74; Cl, 19.54; $H_2O$, 1.60.

I claim:
1. A method for treating leishmaniasis which comprises the step of administering parenterally or orally to an infected animal a leishmanicidally effective amount of a lepidine derivative having the formula:

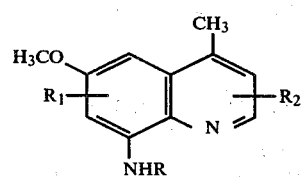

wherein
R represents —$(CH_2)_n$—N(R')(R"), —$(CH_2)_N$—$NH_2$, —CH($CH_3$)—$(CH_2)_3$—$NH_2$;

$R_1$ represents H, —$OCH_3$, —$CH_3$, —$CF_3$, —$C_2H_5$, —CH=$CH_2$—CH=CH—$CH_3$, —$C_3H_7$, —$C_4H_9$,

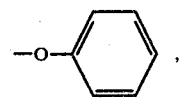

—$C_2H_5$, —CH—$CH_3$ | Br

Cl, or F;

$R_2$ represents H—$CH_3$, —$C_2H_5$, —$CF_3$,

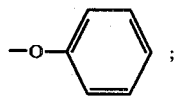

N represents integers 3,4,5,6, or 7; R' and R" represent alkyl or hydrogen; and pharmaceutically acceptable salts thereof wherein the salt forming acid or acid-hydrate is selected from the group consisting of hydrochloric acid, phosphoric acid, nitric acid, sulfamic acid, sulfuric acid, maleic acid, fumaric acid, citric acid, beta-resorcylic acid, and hydrobromic acid.

2. The method of claim 1 wherein the lepidine derivative is selected from the group consisting

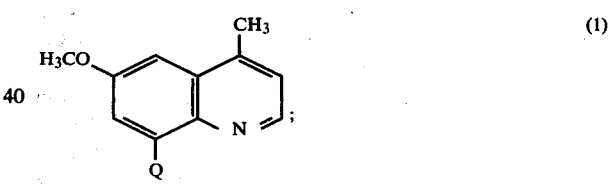

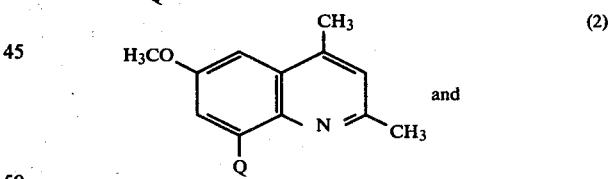

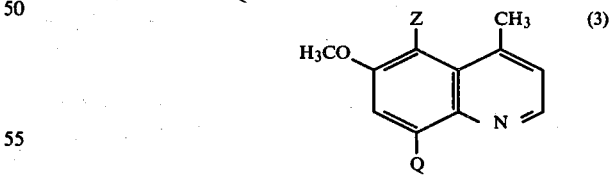

wherein
Q represents —NH($CH_2$)$_n$$NH_2$, —NH($CH_2$)$_x$NHCH($CH_3$)$_2$, —NH($CH_2$)$_t$N($C_2H_5$)$_2$ or —NHCH($CH_3$)($CH_2$)$_3$$NH_2$;
n represents the integers 3,4,5 or 6;
x represents the integers 3,5,6,7 or 8;
t represents the integers 5,6 or 7; and
z represents a halogen or methoxy group.

3. The method of claim 2 wherein the lepidine derivative has the formula

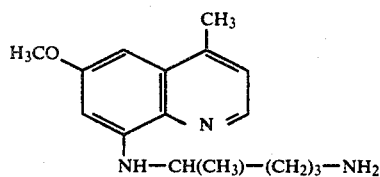

and its corresponding diphosphate salt.

4. The method of claim 2 wherein the lepidine derivative has the formula

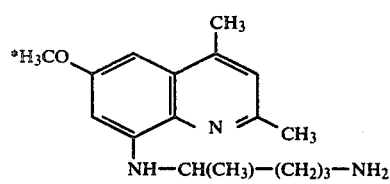

and its corresponding tri (beta-resorcylate salt).

5. The method of claim 2 wherein the lepidine derivative has the formula

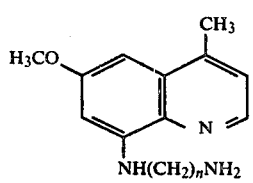

wherein n represents the integers 3 and 6; and their corresponding dihydrochloride salts.

6. The method of claim 2 wherein the lepidine derivative has the formula

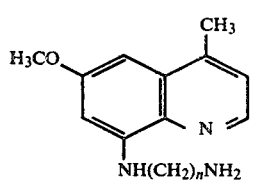

wherein n represents the integers 4 and 5; and their corresponding diphosphate salts.

7. The method of claim 2 wherein the lepidine derivative has the formula

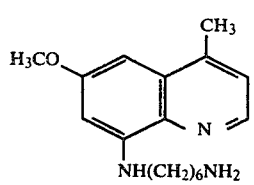

and its corresponding dihydrochloride salt.

8. The method of claim 2 wherein the lepidine derivative has the formula

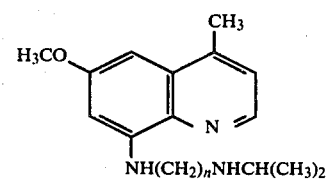

wherein n represents the integers 3,5 and 7; and their corresponding dihydrochloride salt.

9. The method of claim 2 wherein the lepidine derivative has the formula

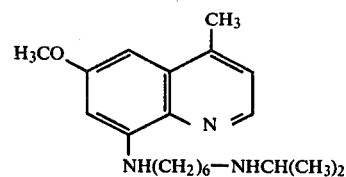

and its corresponding dihydrochloride (mono) hydrate salt.

10. The method of claim 2 wherein the lepidine derivative has the formula

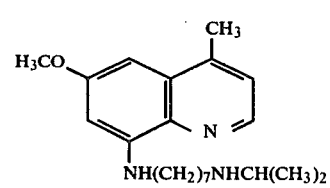

and its corresponding dihydrochloride salt.

11. The method of claim 2 wherein the lepidine derivative has the formula

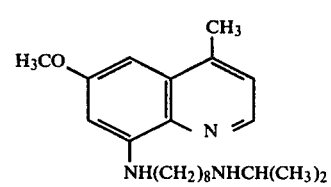

and its corresponding dihydrochloride dihydrate salt.

12. The method of claim 2 wherein the lepidine derivative has the formula

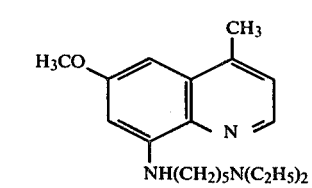

and its corresponding (mono) citrate salt.

13. The method of claim 2 wherein the lepidine derivative has the formula

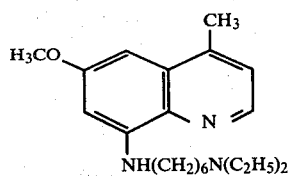

and its corresponding dihydrochloride salt.

14. The method of claim 2 wherein the lepidine derivative has the formula

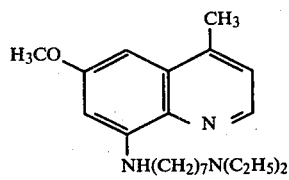

and its corresponding dihydrochloride salt.

15. The method of claim 2 wherein the lepidine derivative has the formula

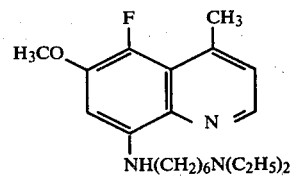

and its dioxalate salt.

16. The method of claim 2 wherein the lepidine derivative has the formula

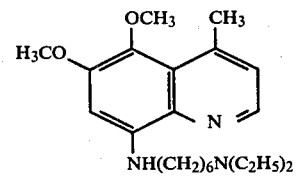

and its dihydrochloride salt.

17. The method of claim 2 wherein the lepidine derivative has the formula

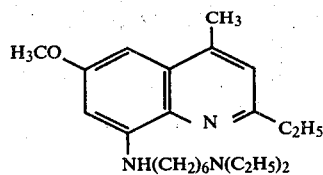

and its corresponding dihydrobromide salt.

18. The method of claim 2 wherein the lepidine derivative has the formula

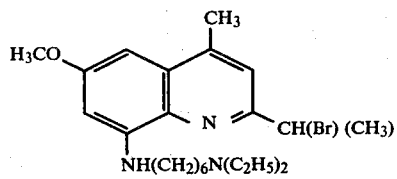

and its corresponding (mono) hydrobromide salt.

19. A method for treating leishmaniasis which comprises the step of administering parenterally or orally to an infected animal a leishmanicidally effective amount of a lepidine derivative having the formula:

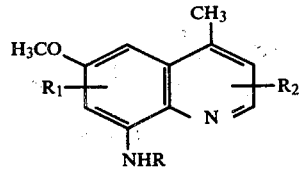

wherein
R represents —alkylene (tertiary) amine, —alkylene—NH$_2$, or —alkylene-secondary amine;
R$_1$ represents an alkoxy, alkyl, halogenated alkyl, alkenyl, aryloxy, halogen or hydrogen radical;
R$_2$ represents hydrogen, alkyl, halogenated alkyl or aryloxy; and pharmaceutically acceptable salts thereof wherein the salt forming acid or acid-hydrate is inorganic or organic in nature.

* * * * *